United States Patent [19]

Backström et al.

[11] Patent Number: 5,292,771

[45] Date of Patent: Mar. 8, 1994

[54] SUBSTITUTED β-DIKETONES AND THEIR USE

[75] Inventors: Reijo J. Backström, Helsinki; Erkki J. Honkanen, Vantaa; Jarmo J. Pystynen, Espoo; Anne M. Luiro, Helsinki; Päivi A. Aho, Helsinki; Inge-Britt Y. Linden, Helsinki; Erkki A. O. Nissinen, Espoo; Pentti Pohto, Helsinki, all of Finland

[73] Assignee: Orion-yhtymä Oy, Espoo, Finland

[21] Appl. No.: 958,487

[22] Filed: Oct. 8, 1992

Related U.S. Application Data

[62] Division of Ser. No. 648,641, Jan. 31, 1991, Pat. No. 5,185,370, which is a continuation-in-part of PCT/FI89/00165, Sep. 1, 1989.

[30] Foreign Application Priority Data

Sep. 1, 1988 [GB] United Kingdom ............... 8820729
Feb. 2, 1990 [GB] United Kingdom ............... 9002337

[51] Int. Cl.$^5$ ............... A61K 31/38; A61K 31/47; A61K 31/44; A61K 31/345
[52] U.S. Cl. ............... 514/472; 514/277; 514/311; 514/352; 514/438; 514/447; 514/461; 514/520; 514/568; 514/620; 514/676; 514/678
[58] Field of Search ............... 514/678, 520, 568, 621, 514/277, 311, 438, 461, 472

[56] References Cited

U.S. PATENT DOCUMENTS

| | | | |
|---|---|---|---|
| 3,280,069 | 10/1966 | Knapp et al. | 260/45.85 |
| 3,856,911 | 12/1974 | Yokotani et al. | 424/331 |
| 3,860,598 | 1/1975 | Rosenkranz et al. | 260/287 R |
| 3,998,872 | 12/1976 | Symon et al. | 260/483 |
| 4,153,719 | 5/1979 | Diana | 568/641 X |
| 4,456,770 | 6/1984 | Everly et al. | 568/315 |

FOREIGN PATENT DOCUMENTS

| | | |
|---|---|---|
| 0008458 | 3/1980 | European Pat. Off. |
| 0052300 | 5/1982 | European Pat. Off. |
| 0308785 | 3/1989 | European Pat. Off. |
| 0323162 | 7/1989 | European Pat. Off. |
| 2155495 | 5/1973 | Fed. Rep. of Germany |
| 2210633 | 9/1973 | Fed. Rep. of Germany |
| 3303066 | 12/1984 | Fed. Rep. of Germany |
| 2607493 | 6/1988 | France |
| 629741 | 5/1982 | Switzerland |
| 2200109 | 7/1988 | United Kingdom |
| WO90/02724 | 3/1990 | World Int. Prop. O. |

OTHER PUBLICATIONS

Korkoiainen, et al.; C.A. 115:255797a (1991).

Toshio Kawato et al, *Bulletin of the Chemical Society of Japan*, vol. 48(3), 1975, "The Chelation of 3-(p-Hydroxybenzylidene-2,4-pentanedione with the Thallous Ion"; pp. 882-884.

Masaaki Iwata et al, *Bulletin of the Chemical Society of Japan*, vol. 49(5), 1976, "Aldol Condensation of Aldehydes with Ketones Promoted by the Copper (II) Ion. Orientation to the Chemical Model for Metalloaldolases"; pp. 1369-1374.

Jean-Paul Vecchionacci et al, *Bulletin Societe Chimique de France*, vol. 7-8, 1974, "Réactions de Friedel et Crafts du benzéne, de l'anisole et du méta-diméthoxybenzéne sur des styrénes β,β-disubstitués par des groupements électroattracteurs"; pp. 1683-1690.

(List continued on next page.)

*Primary Examiner*—Joseph Paul Brust
*Attorney, Agent, or Firm*—Burns, Doane, Swecker & Mathis

[57] ABSTRACT

Compound of formula

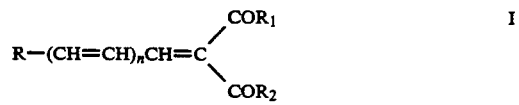

wherein n is 0 or 1, $R_1$ and $R_2$ are independently methyl, ethyl or cyclopropyl and R is an optionally substituted phenyl or heteroaryl group or salt or ester thereof are useful in the treatment of inflammatory bowel disease.

12 Claims, No Drawings

OTHER PUBLICATIONS

Jonathan R. Dimmock et al, *Eur. Journal of Med. Chem.*, vol. 23, No. 2, 1988, "Evaluation of Mannich bases of 2-arylidene-1,3-diketones versus murine P388 leukemia"; pp. 111-117.

Ikuo Katsumi et al, *Chem. Pharm. Bulletin*, vol. 34, No. 4, 1986, "Studies on Styrene Derivatives. II. Synthesis and Antiinflammatory Activity of 3,5-Di-ter-t-butyl-4-hydroxystyrenes", pp. 1619-1627.

Yamashita et al., "The reaction of tetracarbonylhydridoferrate with the knoevenagel condensates of 2,4–pentanedione with aldehydes. A new synthetic route of alkyl methyl ketones from aldehydes," Tetrahedron Letters Nos. 22 and 23, pp. 1867-1868, (1975).

Jiang et al., "Comparison of homologous gradation for isosteric thienyl and phenopolyene series. II," Chemical Abstracts, vol. 108, (1988), 108:149798x.

Pohjala et al., "Electron-impact mass spectra of 2-(-2-pyridyl)methylene-1,3-dicarbonyl compounds. Unusual abundance of the [M+1]+ ion and the effect of stereochemistry," Organic Mass Spectrometry, vol. 16, No. 12, (1981), pp. 519-522.

Solcaniova et al., "Substituent effects on carbon-13 and proton chemical shifts in 3-benzylidene-2,4-pentanediones," Chemical Abstract 198944j. (1982), vol. 96.

Solcaniova et al., "Substituent Effects on $^{13}$C and $^1$H Chemical Shifts in 3-Benzylidene-2,4-pentanediones," Organic Magnetic Resonance, vol. 18, No. 1, (1982), pp. 55-57.

Végh et al., "Synthesis and Reactions of Trimethylammonium Salts of Ethylene Derivatives of Furan," Collection Czechoslovak Chem. Comm., vol. 50, (1985), pp. 1415-1421.

Marchalin et al., "Synthesis of 3-(5-R-2-furylmethylene)pentane-2,4-diones," Chemical Abstracts, vol. 109, (1988); 109:149244j.

Rosado et al., "Mass spectral study of β-dicarbonyl compounds," C. A., vol. 93, (1980), 93:185229t.

Go et al., "The synthesis of 5-methyl-2-furylacetic acid," C.A. vol. 101, (1984), 101:90689n.

Holmberg et al., "Reactions between furfurylidenemalonic esters and Grignard reagents. III. Diethyl 5-methylfurfurylidenemalonate. Isolation of a 1,6-addition product," C.A., 9311x, (1975), vol. 82.

Dimmock et al., "Evaluation of Mannich bases of 2-arylidene-1,3-diketones versus murine P388 leukemia," (1989), C.A., 110:94935y, vol. 110.

Vegh et al., "Ethenyl-2-furyl)-4-aza-1-azoniabicyclo[2.2.2]octane bromode derivatives and their preparation," C.A., vol. 109, (1988), 109:211082k.

Papayan, G. L., "Furan derivatives. XLI. Chloromethylation of furfurylidenemalonates," Chemical Abstracts, vol. 74, (1971), 12913r.

Manrao et al., "Evaluation of ferulic acid derivatives as antifungal agents," Agrochemicals, C.A., vol. 101, (1984), 101:85528e.

Lehnert, W., "Knoevenagel condensation with titanium(IV) chloride-base catalyst V. 3-Alkylidene- and 3-aralkylidene-2,4-pentanedione from aldehydes and acetylacetones," Chemical Abstracts, 169054d, (1975), vol. 82.

Lloyd R. Sutherland, "Medical treatment of inflammatory bowel disease: new therapies, new drugs," *CMAJ*, vol. 137, Nov. 1, 1987, pp. 799-801.

A. S. Arvind and M. J. G. Farthing, "Review: new aminosalicylic acid derivatives for the treatment of inflammatory bowel disease," *Aliment. Pharmacol. Therap.*, (1988), vol. 2, pp. 281-289.

Gerald P. Morris, et al., "Hapten-Induced Model of Chronic Inflammation and Ulceration in the Rat Colon," *Gastroenterology*, Mar. 1989, vol. 96, No. 3, pp. 795-803.

J. E. Lennard-Jones, "Classification of Inflammatory Bowel Disease," pp. 1-6 (publication unknown), (exact date unknown but about 1989).

SUBSTITUTED β-DIKETONES AND THEIR USE

This application is a divisional of application Ser. No. 07/648,641, filed Jan. 31, 1991, now U.S. Pat. No. 5,185,370, which is a continuation-in-part application of PCT/FI89/00165, filed Sep. 1, 1989, which designated the United States.

The present invention relates to substituted β-diketones and their physiologically acceptable salts and esters, which are useful in the treatment of inflammatory bowel diseases.

PCT/FI89/00165 discloses β-diketones, which is herein incorporated by reference, possess cytoprotective efficacy in the stomach and in the duodenum and are useful in the treatment or prophylaxis of gastric and duodenal ulcers.

It has now been found that some substituted β-diketones are especially useful in the treatment of inflammatory bowel diseases (IBD).

The term IBD encompasses chronic inflammatory conditions of the gastrointestinal tract such as Crohn's disease and ulcerative colitis. The exact cause of the disease is still unknown. Infectious agents, immunological abnormalities, permeability disorders and leukotrienes are some of the factors suggested to play a role in the pathogenesis of IBD. The present medical therapy (sulfasalazine, 5-ASA, corticosteroids) is focused only on the diminishing of the inflammatory response, and there is still a great requirement for a more specific and effective drug for the treatment of IBD (Sutherland, CMAJ 137:799–802, 1987).

The present invention provides a method of treatment of inflammatory bowel disease by administering to a patient in need of such treatment an effective amount of a compound of formula I

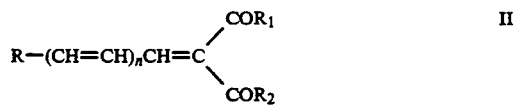

wherein n=0 or 1, $R_1$ and $R_2$ are independently methyl, ethyl or cyclopropyl and R is an optionally substituted phenyl or heteroaryl group;

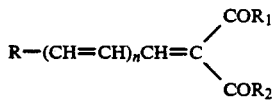

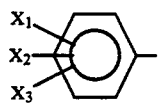 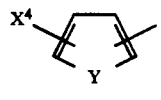

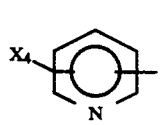 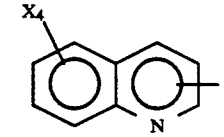

wherein $X_1$ is hydrogen, hydroxy or alkoxy which is optionally substituted by aryl; $X_2$ and $X_3$ are independently hydrogen, nitro, cyano, halo, trifluoromethyl, formyl, carboxy, acetamido or;

wherein m=0, 1 or 2 and $R_3$ is alkyl, aryl or aralkyl; or carbamoyl which is optionally substituted by alkyl, aryl or aralkyl; Y is oxygen or sulfur and $X_4$ is hydrogen, nitro or halo; or a pharmaceutically acceptable salt or ester thereof.

The present invention also provides a compound according to the general formula II

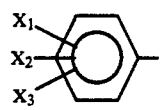

wherein n=0 or 1, $R_1$ is methyl, ethyl or cyclopropyl and $R_2$ is ethyl or cyclopropyl and R is

wherein $X_1$ is hydrogen, hydroxy or alkoxy which is optionally substituted by aryl; $X_2$ and $X_3$ are independently hydrogen, nitro, cyano, halo, trifluoromethyl, formyl, carboxy, acetamido or;

$R_3S(O)_m$— wherein m=0, 1 or 2 and $R_3$ is alkyl, aryl or aralkyl; or carbamoyl which is optionally substituted by alkyl, aryl or aralkyl or $R_1$ and $R_2$ are methyl and R is

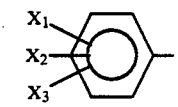

where $X_1$, $X_2$ and $X_3$ are as defined above provided that one of $X_2$ and $X_3$ is carbamoyl which is optionally substituted by alkyl, aryl or aralkyl, or a pharmaceutically acceptable salt or ester thereof.

The invention also provides a new compound according to the general formula III

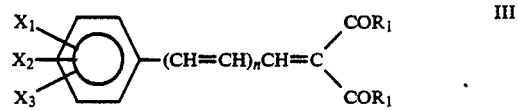

wherein n is 0 or 1, $R_1$ is methyl and $X_1$ is as defined above and $X_2$ is

wherein m is 1 or 2 and $R_3$ is alkyl, aryl or aralkyl and $X_3$ is hydrogen, nitro, cyano, halo, trifluoromethyl, formyl, carboxy or a group as defined for $X_2$; or $X_2$ and $X_3$ are both nitro or cyano; or $X_2$ is nitro and $X_3$ is formyl or halo or, when $X_1$ is hydroxy, $X_2$ may be carboxy, or $X_2$ and $X_3$ may both be hydrogen when n=0 and $X_1$ is alkoxy substituted by aryl, or when n=1 and $X_1$ is hydroxy or alkoxy optionally substituted by aryl; or a pharmaceutically acceptable salt or ester thereof but excluding 3-[(2-chloro-5-nitrophenyl)methylene]-2,4-pentanedione.

The term "alkyl" as employed herein refers to an alkyl group having preferably 1 to 2 carbon atoms.

The term "alkoxy" as employed herein refers to an alkyl residue as defined above linked to an oxygen atom.

The term "aralkyl" as employed herein refers to an alkyl group having aryl, preferably phenyl as the substituent.

The term "aryl" refers to a carbocyclic aromatic group containing form 6 to 10 carbon atoms in the ring portion. The group may be a single ring or fused rings. Specific examples are phenyl and naphthyl.

The term "heteroaryl" refers to monocyclic or bicyclic aromatic group containing one or more heteroatoms such as nitrogen, oxygen or sulfur.

The preparation of compounds according to the formulae I and II may be carried out in a similar way as described in PCT/FI89/00165 For example the compounds of formula I may be prepared by reacting a compound of the formula IV

$R_1-CO-CH_2-CO-R_2$    IV in which $R_1$ and $R_2$ are as defined above with a compound of formula V

$R-(CH=CH)_n-Z$    V in which n and R are as defined above and Z is CHO or $-CH_2-Q$, wherein Q is halogen or some other activated group, in the presence of acidic or basic catalyst to produce a compound of formula I or a compound of formula VI

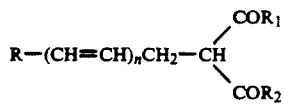

in which n, $R_1$, $R_2$ and R are as defined above, which compound is halogenated to give a compound of the formula VII

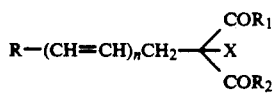

in which n, $R_1$, $R_2$ and R are as defined above and X is halogen and dehydrohalogenating compound VII to produce a compound of the formula I.

The basic catalyst may be for example an organic or inorganic base. The acidic catalyst may be for example a mineral or sulfonic acid. The activated group Q may be a halogen or an alkyl or aryl sulfonate.

When halogenating a compound of formula VI elementary halogen, preferably chlorine or bromine may be used, or another known halogenating agent such as sulfuryl chloride may be used.

Salts of these compounds may be prepared by known methods. Most commonly used pharmaceutically acceptable salts are sodium, potassium, ammonium, calcium and magnesium salts and hydrochlorides or hydrobromides. Preferred esters of the compounds of formula I are acyl or aroyl derivatives which will hydrolyse under physiological conditions.

The above compounds may be formulated to dosage forms using the principles which are known to those having average skill in the art. Suitable solvents, gel forming ingredients, dispersion agents, antioxidants and colorants may be added in a normal way.

It is preferred to administer the compounds enterally. When they are given orally, they may be in the form of tablets, granules, capsules, emulsions, suspensions or solutions. It is often advisable to use coated tablets or granules, i.e. so called enterocoated preparations, to ensure that the medicine reaches the desired part of the gastrointestinal tract. Alternatively, the compositions may be given rectally in the form of enemas or suppositories.

The effective dose varies considerably depending on location, degree and severity of the disease being treated as well as the age and the general condition of the patient. The effective dose is generally from about 20 to 1000 mg per day, preferably from 50 to 250 mg per day for an adult, once a day or divided into two to five doses.

In Vivo Tests

The efficacy of the compounds can be demonstrated by using a model of chronic colonic inflammation in the rat, TNB-induced chronic colitis. TNB-induced chronic colonic inflammation in rats is an animal model which has been shown to resemble human IBD.

20 mg of TNB (2,4,6-trinitrobenzenesulfonic acid) in 50% ethanol was administered into the lumen of the colon via a rubber catheter inserted rectally to Wistar rats. The test compounds were given rectally 1 h prior and 24, 48, 72 and 95 h after TNB. The rats were sacrificed 96 h after TNB and their colons were scored according to occurence of ulcers and inflammation. The number of animals in each group was at least 8. 5-ASA (5-aminosalicylic acid), a clinically used drug for the treatment of IBD was used as a reference compound. The results are presented in the Table 1.

TABLE 1

The effect of test compounds on the damage score of chronic inflammation induced by TNB.

| Test compound | Dose mg/kg | % inhibition against control |
|---|---|---|
| 5-ASA | 100 | 24 |
| 1 | 30 | 37 |
| 2 | 30 | 28 |
| 3 | 10 | 18 |
|   | 30 | 57 |
| 4 | 30 | 54 |
| 5 | 30 | 43 |
| 6 | 30 | 41 |
| 7 | 10 | 60 |
|   | 30 | 48 |
| 8 | 10 | 51 |
|   | 30 | 62 |
| 9 | 30 | 40 |
| 10 | 10 | 27 |
| 11 | 30 | 32 |
| 12 | 30 | 52 |
| 13 | 30 | 58 |
| 14 | 30 | 30 |

Test Compounds 1 3-(4-hydroxyphenyl)methylene-2,4-pentanedione
2 3-(4-methoxyphenyl)methylene-2,4-pentanedione
3 3-(3-nitrophenyl)methylene-2,4-pentanedione
4 3-(4-trifluoromethylphenyl)methylene-2,4-pentanedione
5 3-(4-nitrophenyl)methylene-2,4-pentanedione
6 3-(2-nitrophenyl)methylene-2,4-pentanedione
7 3-(4-cyanophenyl)methylene-2,4-pentanedione
8 3-(3-cyanophenyl)methylene-2,4-pentanedione
9 3-[(4-(N-phenethyl)carboxamido-phenyl)methylene]-2,4-pentanedione
10 3-[(5-nitrofuryl)methylene]-2,4-pentanedione
11 4-[(4-cyanophenyl)methylene]-3,5-heptanedione 12 2-[(4-cyanophenyl)methylene]-1,3-dicyclopropyl-1,3-propanedione 13 2-[(3-trifluoromethylphenyl)methylene]-1,3-dicyclopropyl-1,3-propanedione 14 2-[(4-carboxyphenyl)methylene]-1,3-dicyclopropyl-1,3-propanedione The test compounds significantly decreased the ulceration and inflammation of the colons. The test compounds were much more potent than the reference compound 5-ASA and should therefore be more effective than 5-ASA in the treatment of human IBD.

The following examples illustrate the production of compounds of use according to the invention.

EXAMPLE 1

3-[(4-Phenylsulfonylphenyl)methylene]-2,4-pentanedione

To a solution containing 2.1 g of 4-phenylsulfonylbenzaldehyde and 1.5 g of 2,4-pentanedione in 10 ml of 2-propanol was added 1 ml of thionyl chloride with stirring at 20° C. The solution was stirred for 1 h at 20° C. and evaporated to dryness in vacuo. The residue was crystallized from toluene, mp 102°–105° C.

EXAMPLE 2

3-[(4-Methylsulfonylphenyl)methylene]-2,4-pentanedione

The procedure described in Example 1 was repeated by using 1.1 g of 4-methylsulfonylbenzaldehyde and 1.5 g of 2,4-pentanedione. The product was crystallized from ether, mp 139°–140° C.

EXAMPLE 3

3-[(4-Carboxamidophenyl)methylene]-2,4-pentanedione

A mixture containing 1.8 g of 4-carboxamidobenzaldehyde, 1.1 g of 2,4-pentanedione, 0.2 g of piperidine and 0.2 g of acetic acid in 40 ml of toluene was refluxed for 3 h by using a Dean-Stark separator. The warm clean toluene solution was decanted from the tarry residue and cooled. The crystalline product was filtered and dried. Mp 154°–155° C.

EXAMPLE 4

4-[(4-Nitrophenyl)methylene]-3,5-heptanedione

The procedure described in Example 1 was repeated by using 1.5 g of 4-nitrobenzaldehyde and 2.0 g of 3,5-heptanedione. Yield 1.7 g, yellow oil.

EXAMPLE 5

3-[(3,4-Dichlorophenyl)methylene]-2,4-pentanedione

The procedure described in Example 1 was repeated by using 4.26 g of 3,4-dichlorobenzaldehyde and 3.0 g of 2,4-pentanedione. Yield 1.3 g, mp 73° C.

EXAMPLE 6

3-[(4-Chloro-3-nitrophenyl)methylene]-2,4-pentanedione

The procedure described in Example 1 was repeated by using 1.85 g of 4-chloro-3-nitrobenzaldehyde and 1.5 g of 2,4-pentanedione. Yield 1.32 g, mp 110°–111° C.

EXAMPLE 7

3-[(4-(N-phenethyl)carboxamidophenyl)methylene]-2,4-pentanedione.

The procedure described in Example 1 was repeated by using 2.5 g of 4-(N-phenethyl)carboxamidobenzaldehyde and 1.0 g of 2,4-pentanedione. Yield 0.5 g, mp 146°–149° C.

EXAMPLE 8

3-[(4-Formyl-3-nitrophenyl)methylene]-2,4-pentanedione

To a solution containing 1.84 g of 2-nitroterephtaldicarboxaldehyde and 1.00 g of 2,4-pentanedione in 10 ml trifluoroacetic acid were added 0.9 ml of thionyl chloride and a catalytic amount of water. The solution was stirred for 2 h at 20° C. 30 ml of water was added and the mixture was extracted with ether. The ether extract was washed several times with $Na_2CO_3$-solution and dried over $K_2CO_3$. After filtration the solvent was evaporated in vacuo. The product was purified by column chromatography. Yield 0.2 g, mp 102°–104° C.

EXAMPLE 9

3-[(3,5-Dinitro-4-hydroxyphenyl)methylene]-2,4-pentanedione.

The procedure described in Example 1 was repeated by using 2.12 g of 3,5-dinitro-4-hydroxybenzaldehyde and 1.5 g of 2,4-pentanedione. Yield 1.9 g, mp 158° C.

EXAMPLE 10

3-1(3,5-Dinitrophenyl)methylene]-2,4-pentanedione

The procedure described in Example 1 was repeated by using 2.53 g 3,5-dinitrobenzaldehyde and 2.43 g of 2,4-pentanedione. Yield 0.8 g, mp 101°–105° C.

EXAMPLE 11

3-[3-(4-Methoxyphenyl)propenylene]-2,4-pentanedione

To a solution containing 2.45 g of 4-methoxycinnamaldehyde in 90 ml of toluene was added 2.2 g of 2,4-pentanedione, 0,26 g of piperidine and 0.45 9 of acetic acid. The solution was refluxed in $N_2$ atmosphere for 1 h and the water formed in the reaction was azeotropically distilled off by using a Dean-Stark water separator. The solution was evaporated to dryness in vacuo. The residue was trifurated with ether. The crystals were filtered. Yield 0.65 g, mp 108°–110° C.

EXAMPLE 12

3-[(S-Nitrofuryl)methylene]-2,4-pentanedione

A solution containing 2.43 g of 5-nitro-2-furanecarboxaldehyde diacetate, 1.5 g of 2,4-pentanedione and 0.1 g of water in 5 ml of tetrahydrofurane was saturated with hydrogen chloride gas at 20° C. The mixture was stirred for 1 h and evaporated to dryness in vacuo. The product was recrystallized from acetic acid. Yield 0.1 g, mp 117°–120° C.

EXAMPLE 13

3-[(S-Nitrothienyl)methylene]-2,4-pentanedione

The procedure described in Example 12 was repeated by using 2.59 g of 5-nitro-2-thiophenecarboxaldehyde diacetate, 1.5 g of 2,4-pentanedione. Yield 0.5 g, yellow viscous oil.

EXAMPLE 14

3-(3-Pyridylmethylene)-2,4-pentanedione

The procedure described in Example 3 was repeated by using 3.21 g of pyridine-3-carboxaldehyde and 3.3 g of 2,4-pentanedione. Yield 2.95 g, mp 52°–57° C.

EXAMPLE 15

3-(4-Pyridylmethylene)-2,4-pentanedione hydrochloride

A solution containing 1.1 g of pyridine-4-carboxaldehyde and 1.0 g of 2,4-pentanedione in 10 ml of N,N-dimethylformamide was saturated with hydrogen chloride gas at 20° C. The solution was stirred for 1 h at 20° C. and then for 2 h at 80° C. The solvent was evaporated in vacuo and the residue was crystallized from ethanol. Yield 0.17 g, mP 175°-186° C.

EXAMPLE 16

3-(3-Quinolylmethylene)-2,4-pentanedione hydrochloride

The procedure described in Example 3 was repeated by refluxing 2.4 g quinoline-3-aldehyde, 6.6 g 2,4-pentanedione, 0.4 g piperidine and 0.8 g acetic acid in 100 ml toluene. Yield 1.4 g, mp 99°-101° C.

EXAMPLE 17

3-[(3-Carboxy-4-hydroxyphenyl)methylene]-2,4-pentanedione

A mixture containing 2 g 3-carboxy-4-hydroxybenzaldehyde, 4 ml 2,4-pentanedione and 20 ml tetrahydrofuran was saturated with hydrogen chloride gas. The solution was stirred for 2.0 h at 50° C. and evaporated to dryness in vacuo. The residue was crystallized from ethyl ether, mp. 112°-114° C.

EXAMPLE 18

3-[[(4-(2-Phenylethoxy)phenyl]methylene]-2,4-pentanedione

The procedure described in example 8 was repeated by using 5.9 g of 4-(2-phenylethoxy)benzaldehyde, 3.9 ml of 2,4-pentanedione, 26 ml of trifluoroacetic acid and 2.1 ml of thionyl chloride. Yield 4.7 91 an viscous oil.

EXAMPLE 19

2-[(4-Acetamidophenyl)methylene]-1,3-dicyclopropyl-1,3-propanedione

A mixture containing 1.6 g 4-acetamidobenzaldehyde, 1.5 g 1,3-dicyclopropyl-1,3-propanedione, 0.2 ml of piperidine and 0.4 ml of acetic acid in 50 ml of toluene was refluxed for 3 h by using a Dean-Stark separator. After standing over night at room temperature the crystals were filtered and washed with toluene. The product was recrystallized from ethanol. Yield 2.0 g, mp 166°-167° C.

EXAMPLE 20

2-[(4-Methoxyphenyl)methylene]-1,3-dicyclopropyl-1,3-propanedione

The procedure described in Example 19 was repeated by using 0.68 g 4-methoxybenzaldehyde and 0.77 g 1,3-dicyclopropyl-1,3-propanedione. Yield 0.46 g, mp 60.5°-61.5° C.

EXAMPLE 21

4-[(3-Cyano phenyl)methylene]-3,5-heptanedione

The procedure described in Example 19 was repeated by using 1.82 g 3-cyanobenzaldehyde and 3.5 g 3,5-heptanedione. Yield 0.4 g, mp 51°-52° C.

EXAMPLE 22

4-1(4-Cyanophenyl)methylene]-3,5-heptanedione

The produre described in Example 19 was repeated by using 2.6 g 4-cyanobenzaldehyde and 5.0 g 3,5-heptanedione. Yield 2.8 g, mp 59°-60° C.

EXAMPLE 23

3-[(4-Cyanophenyl)methylene]-4-cyclopropyl-2,4-butanedione

The procedure described in Example 19 was repeated by using 2.6 g 4-cyanobenzaldehyde and 2.5 g 4-cyclopropyl-2,4-butanedione. The product was purified by column chromatography. Yield 0.37 g, mp 83°-85° C.

EXAMPLE 24

2-[(4-Cyanophenyl)methylene]-1,3-dicyclopropyl-1,3-propanedione

The procedure described in Example 19 was repeated by using 3.78 g 4-cyanobenzaldehyde and 2.23 g 1,3-dicyclopropyl-1,3-propanedione. Yield 1.5 9, mp 100°-102° C.

EXAMPLE 25

3-[(5-Bromothienyl)methylene]-2,4-pentanedione

To a solution containing 5.73 g 5-bromothiophene-2-carboxaldehyde and 5.0 g 2,4-pentanedione in 25 ml of 2-propanol, 2.9 ml thionylchloride was gradually added. The mixture was stirred for 2 h at 20° C. 120 ml of conc. $Na_2SO_4$-solution was then added and the mixture was extracted with ether. The solvent was evaporated in vacuo and the crystalline residue was washed with cold ether. Yield 3.9 g, mp 70°-74° C.

EXAMPLE 26

2-[(3-Trifluoromethylphenyl)methylene]-1,3-dicyclopropyl-1,3-2-propanedione

The procedure described in Example 19 was repeated by using 2.15 ml 3-trifluoromethylbenzaldehyde and 2.42 g 1,3-dicyclopropyl-1,3-propanedione. Yield 2.71 g, mp 56°-58° C.

EXAMPLE 27

2-[(4-Carboxyphenyl)methylene]-1,3-dicyclopropyl-1,3-propanedione

The procedure described in Example 19 was repeated by using 3.0 g 4-carboxybenzaldehyde and 3.06 g 1,3-dicyclopropyl-1,3-propanedione. Yield 1.7 g, mp 175°-178° C. in trifluoroacetic acid (10 ml) thionylchloride (4 ml) and catalytic amount of water (0,05 ml) were added at room temperature. The solution was stirred over right at 20° C. The solvent was evaporated and the residue was destilled in vacuo, bp 110° C./1,5 mbar. Yield 5,3 g (41%).

EXAMPLE 28

3-(4-Trifluoromethylbenzylidene)-2,4-pentanedione

4-Trifluoromethylbenzaldehyde (8,7 g) was condenced with 2,4-pentanedione (5,01 g in trifluoroacetic acid (10 ml) thionylchloride (4 ml) and catalytic amount of water (0,05 ml) were added at room temperature. The solution was stirred over right at 20° C. The solvent was evaporated and the residue was destilled in vacuo, bp 110° C./1,5 mbar. The crude product was crystallized from a mixture of ether-petroleum ether (1:1), mp 46°-48° C., yield 3,8 g (30 %).

EXAMPLE 29

3-(3-Cyanobenzylidene)-2,4-pentanedione 3-cyanobenzaldehyde (2,62 g) was condenced with 2,4-pentanedione (3,0 g) in 2-propanol (10 ml) in the presence of ammonium acetate. Mp 63°-64° C., yield 1,27 g (30%).

EXAMPLE 30

3-(4-Cyanobenzylidene)-214-pentanedione

4-Cyanobenzaldehyde (2,62 g) was condenced with 2,4-pentanedione (3,0 g) in 2-propanol (10 ml) in the presence of ammonium acetate. Mp 86°-88° C., yield 0,55 g (13%).

We claim:

1. A method of treatment of inflammatory bowel disease by administering to a patient in need of such treatment a therapeutically effective amount of the compound of formula I

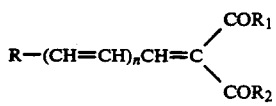

wherein n is 0 or 1, $R_1$ and $R_2$ are independently methyl, ethyl or cyclopropyl and R is an unsubstituted or substituted phenyl;

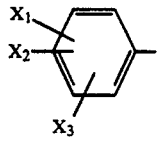

wherein $X_1$ is hydrogen, hydroxy or $C_{1-2}$ alkoxy which is unsubstituted or substituted by carbocyclic aryl; $X_2$ and $X_3$ are independently hydrogen, nitro, cyano, halo, trifluoromethyl, formyl, carboxy, acetamido, or the group

wherein m is 0, 1 or 2 and $R_3$ is $C_{1-2}$ alkyl, carbocyclic aryl or carbocyclic aryl $C_{1-2}$ alkyl; or carbamoyl which is unsubstituted or substituted by $C_{1-2}$ alkyl, carbocyclic aryl $C_{1-2}$ alkyl, aryl, or R is one of the following heteroaryl groups;

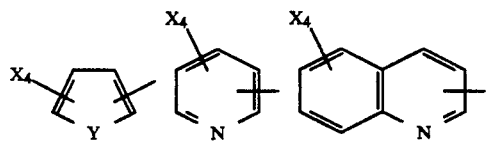

wherein Y is oxygen or sulfur and $X_4$ is hydrogen, nitro or halo; or a pharmaceutically acceptable salt or ester thereof to treat inflammatory bowel disease.

2. The method according to claim 1, in which, in the compound of formula I, $X_1$ is hydroxy or alkoxy.

3. The method according to claim 1, in which, in the compound of formula I, one of $X_2$ and $X_3$ is nitro, cyano, trifluoromethyl, carboxy or carbamoyl which is substituted by carbocyclic aryl.

4. The method according to claim 1, wherein the compound is selected from the group comprising
3-(4-hydroxyphenyl)methylene-2,4-pentanedione,
3-(4-methoxyphenyl)methylene-2,4-pentanedione,
3-(3-nitrophenyl)methylene-2,4-pentanedione,
3-(4-nitrophenyl)methylene-2,4-pentanedione,
3-(2-nitrophenyl)methylene-2,4-pentanedione,
3-[(4-(N-phenethyl)carboxamido-phenyl)methylene]-2,4-pentanedione,
3-[(5-nitrofuryl)methylene]-2,4-pentanedione, and
2-[(4-carboxyphenyl)methylene]-1,3-dicyclopropyl-1,3-propanedione or a pharmaceutically acceptable salt or ester thereof.

5. The method according to claim 1, wherein the compound is 3-(4-trifluoromethylphenyl)methylene-2,4-pentanedione.

6. The method according to claim 1, wherein the compound is 3-(4-cyanophenyl)methylene-2,4-pentanedione.

7. The method according to claim 1, wherein the compound is 3-(3-cyanophenyl)methylene-2,4-pentanedione.

8. The method according to claim 1, wherein the compound is 4[(4-cyanophenyl)methylene]-3,5-heptanedione.

9. The method according to claim 1, wherein the compound is 2-[(4-cyanophenyl)methylene]-1,3-dicyclopropyl-1,3-propanedione.

10. The method according to claim 1, wherein the compound is 2-[(3-trifluoromethylphenyl)methylene]-1,3-di-cyclopropyl-1,3-propanedione.

11. The method according to claim 1, wherein the inflammatory bowel disease is ulcerative colitis.

12. The method according to claim 1, wherein the inflammatory bowel disease is Crohn's disease.

* * * * *